(12) United States Patent
Allbritton et al.

(10) Patent No.: US 11,920,115 B2
(45) Date of Patent: Mar. 5, 2024

(54) ARRAY OF MICRO-ELEMENTS FOR HIGH RESOLUTION AND HIGH CONTENT IMAGING AND SORTING OF CELLS

(71) Applicants: The University of North Carolina at Chapel Hill, Chapel Hill, NC (US); Cell Microsystems, Inc., Research Triangle Park, NC (US)

(72) Inventors: Nancy L. Allbritton, Chapel Hill, NC (US); Yuli Wang, Cary, NC (US); Christopher E. Sims, Chapel Hill, NC (US); Nicholas C. Dobes, Durham, NC (US); Steven C. Gebhart, Durham, NC (US); Nicholas C. Trotta, Durham, NC (US)

(73) Assignees: The University of North Carolina at Chapel Hill, Chapel Hill, NC (US); Cell Microsystems, Inc., Research Triangle Park, NC (US)

( * ) Notice: Subject to any disclaimer, the term of this patent is extended or adjusted under 35 U.S.C. 154(b) by 0 days.

(21) Appl. No.: 16/116,611

(22) Filed: Aug. 29, 2018

(65) Prior Publication Data
US 2019/0136170 A1    May 9, 2019

Related U.S. Application Data

(63) Continuation of application No. PCT/US2017/019889, filed on Feb. 28, 2017.
(Continued)

(51) Int. Cl.
*C12M 1/00* (2006.01)
*C12M 1/12* (2006.01)
(Continued)

(52) U.S. Cl.
CPC ............ *C12M 23/20* (2013.01); *C12M 23/12* (2013.01); *C12M 23/26* (2013.01); *C12M 25/04* (2013.01); *C12M 41/36* (2013.01)

(58) Field of Classification Search
CPC ...... C12M 23/12; C12M 23/20; C12M 23/26; C12M 25/04; C12M 41/36
See application file for complete search history.

(56) References Cited

U.S. PATENT DOCUMENTS 5,128,204 A * 7/1992 Charmot .................... C08J 3/20
                                                     252/62.56
5,178,947 A    1/1993 Charmot et al.
(Continued)

FOREIGN PATENT DOCUMENTS

EP    1223149 A1    7/2002
JP    3888613 B2 *  3/2007
(Continued)

OTHER PUBLICATIONS

IPRP with International Search Report and Written Opinion corresponding to International Application No. PCT/US2017/019889 dated Sep. 4, 2018.
(Continued)

*Primary Examiner* — William H. Beisner
(74) *Attorney, Agent, or Firm* — KDW FIRM PLLC

(57) ABSTRACT

An array of magnetic or paramagnetic micro-elements comprised of polysilsesquioxane is described having ultra-low-autofluorescence and other optical properties to improve microscopic imaging of cells or other objects present on the array. These materials are also amenable to chemical modification allowing surface attachment of affinity capture moieties or chemical reporters for selective binding or analysis of cells, macromolecules or other targets.

11 Claims, 10 Drawing Sheets

Related U.S. Application Data

(60) Provisional application No. 62/300,983, filed on Feb. 29, 2016.

(51) Int. Cl.
  *C12M 1/32* (2006.01)
  *C12M 1/34* (2006.01)

(56) References Cited

U.S. PATENT DOCUMENTS

| | | | |
|---|---|---|---|
| 7,282,241 B2* | 10/2007 | Kim et al. | G01N 33/54393 427/508 |
| 7,907,809 B2* | 3/2011 | Korampally et al. | C01B 33/145 385/123 |
| 9,068,155 B2 | 6/2015 | Allbritton et al. | |
| 2002/0090739 A1* | 7/2002 | Laguitton | C03C 17/30 436/518 |
| 2003/0055193 A1* | 3/2003 | Lichtenhan | C08G 77/24 528/10 |
| 2009/0269016 A1* | 10/2009 | Korampally | G02B 6/0229 977/773 |
| 2012/0237677 A1 | 9/2012 | Korampally et al. | |
| 2013/0065795 A1* | 3/2013 | Allbritton et al. | C12M 23/12 506/26 |
| 2015/0210972 A1 | 7/2015 | Allbritton et al. | |
| 2015/0283543 A1* | 10/2015 | McKean | C12M 25/14 435/396 |
| 2019/0032007 A1* | 1/2019 | Mckean | C12N 5/0075 |

FOREIGN PATENT DOCUMENTS

| WO | WO 2007/008440 A2 | 1/2007 |
|---|---|---|
| WO | WO 2011/103143 A1 | 8/2011 |

OTHER PUBLICATIONS

Wang et al. "Simple Ligand Exchange Reactions Enabling Excellent Dispersibility and Stability of Magnetic Nanoparticles in Polar Organic, Aromatic, and Protic Solvents," Langmuir, vol. 30, pp. 1514-1521 (2014).

* cited by examiner

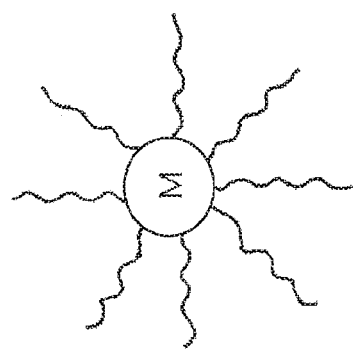
In Toluene
Ligand Exchange
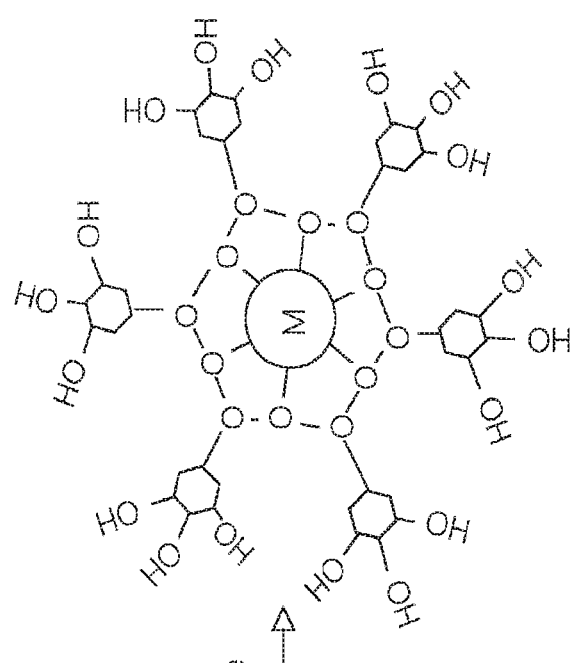
In GBL
FIG. 4A
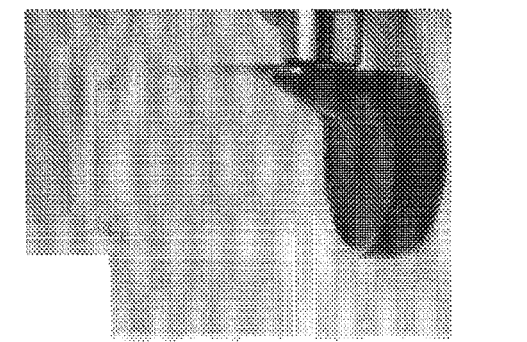
FIG. 4B

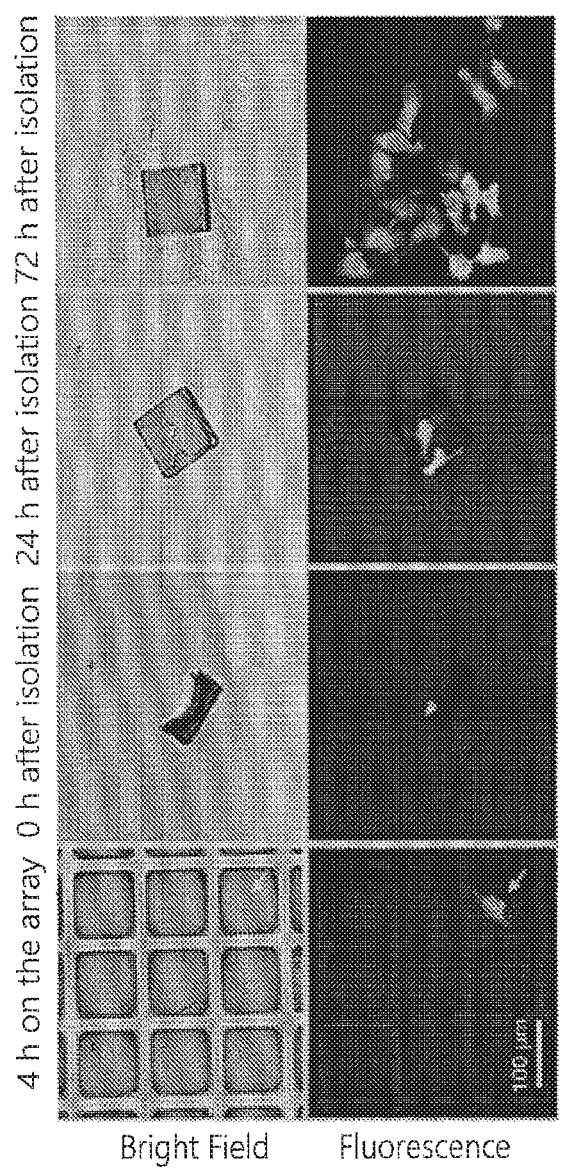

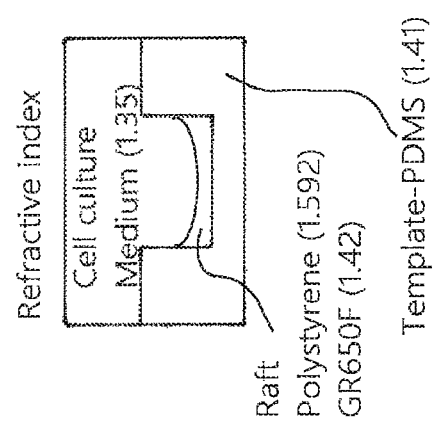
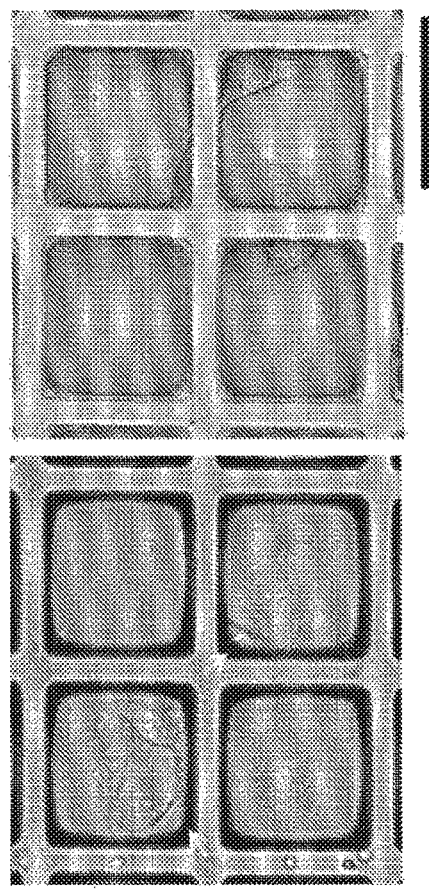
FIG. 8A  FIG. 8B  FIG. 8C

ARRAY OF MICRO-ELEMENTS FOR HIGH RESOLUTION AND HIGH CONTENT IMAGING AND SORTING OF CELLS

CROSS-REFERENCE TO RELATED APPLICATIONS

This application is a continuation of PCT International Patent Application Serial No. PCT/US2017/019889, filed Feb. 28, 2017, which itself claims the benefit of United States Provisional Patent Application Ser. No. 62/300,983, filed Feb. 29, 2016. The contents of each of these applications are incorporated herein by reference in their entireties, and the benefit of the filing date of the provisional application is hereby claimed for all purposes that are legally served by such claim for the benefit of the filing date.

GOVERNMENT INTEREST

This invention was made with government support under Grant Number EB017549 awarded by the National Institutes of Health. The government has certain rights in the invention.

BACKGROUND

Prior embodiments of an array of micro-elements as cell carriers were composed of micron-scale polystyrene elements, each termed a "microraft", doped with ferromagnetic nanoparticles. Within the array, the microrafts serve as releasable culture sites or cell carriers for individual cells or colonies. Cells are plated on the array in the same manner as a Petri dish, and the cells remain positioned on specific microrafts while in culture so that single cells can expand into clonal colonies or obtained as isolated single cells or colonies for further analysis. Analysis of the individual cell or colony can take place at one or multiple time points, dramatically expanding the potential criteria used for selection. In one embodiment target cells or colonies are isolated using a probe which is pushed through the compliant polydimethylsiloxane (PDMS) substrate to dislodge a microraft and its attached cell or colony. Upon release, the individual microraft carrier with its attached cell or colony is collected by a magnetic wand and delivered to a separate vessel. This strategy achieves cell isolation with excellent viability and purity; for example, single-cell cloning efficiencies of greater than 95% have been realized with 100% purity.

There are many advantages of using polystyrene to create microrafts. Polystyrene is the material frequently used for manufacturing cell culture devices (e.g. petri dishes, multi-well plates). Polystyrene is well known as a biocompatible material for cell culture. Once plasma treated, the surface properties of polystyrene are stable for a shelf life of up to several years. Polystyrene can be stably mixed with ferromagnetic nanoparticles by introducing a small moiety of acrylic acid to the polystyrene chain. Polystyrene can be dissolved in gamma-butyrolactone (GBL), a solvent that does not swell elastomeric materials such as PDMS that are used to fabricate array substrates.

Although polystyrene has the above advantages, it has distinct limitations, one of which is substantial autofluorescence at blue and green wavelengths. This range of wavelength overlaps many common fluorophores used in life science research such as fluorescein isothiocyanate (FITC), green fluorescent protein (GFP), Alexa Fluor 488, rhodamine B, etc. The autofluorescence of micro-elements made from polystyrene interferes and blurs the imaging of cells grown on their upper surface, especially for subcellular structures which emit a relatively low level of fluorescent signal using the standard tools available to life science researchers. In addition, the refractive index of polystyrene differs significantly from the refractive index of elastomeric materials such as PDMS that are used to form the substrate of an array. This results in the refraction of light across multiple, disparate indices as the light passes from the source to the observer, thereby resulting in reduced image quality or signal intensity. Also, the transparency of polystyrene at light wavelengths near or below the low end of the visible spectrum can be diminished. Therefore, micro-elements with improved optical properties, including ultra-low autofluorescence, would greatly benefit high-resolution and high-content imaging of subcellular structures of live cells on the microraft arrays. Also, adding a capability to undergo chemical modification allowing the covalent attachment of biological or chemical moieties both at the time of fabrication or immediately prior to an experiment would further expand the uses of microraft arrays for cell studies.

SUMMARY

A first aspect of the invention is an apparatus for collecting or culturing cells or cell colonies. The apparatus comprises a substrate formed from a flexible resilient polymeric material and having a first surface and an opposed second surface and a plurality of wells formed in the first surface in the form of an array; and a plurality of micro-elements releasably connected to the substrate. The micro-elements of the invention comprise a polysilsesquioxane having improved properties for imaging resulting from low autofluorescence of the micro-element and refractive indices of the micro-element and the substrate that are closely matched. The micro-element may further comprise ferromagnetic particles.

In some embodiments the substrate comprises an elastomer. The elastomer in some embodiments is polydimethylsiloxane.

In some embodiments, the polysilsesquioxane is a thermosetting polysilsesquioxane resin. The polysilsesquioxane resin in some embodiments is polymethylsilsesquioxane.

The micro-elements of the invention may be functionalized with a silane coupling reagent having the general formula R—Si(R')$_3$, where R' can be one or more of OH, Cl or alkoxyl and where R has a terminal functional group comprising an epoxide, amine, carboxyl, vinyl, mercapto, or imine. The R-terminal functional group may in some embodiments be covalently bound to a biologically or chemically active moiety.

A further aspect of the invention is a method of collecting cells or cell colonies, comprising providing an apparatus having improved properties for imaging. The apparatus comprises a substrate formed from an elastomer and having a first surface and an opposed second surface and a plurality of wells formed in the first surface in the form of an array, and a plurality of micro-elements having low autofluorescence and a refractive index closely matched to the refractive index of the substrate, each micro-element disposed in one of the wells and configured to release from the substrate upon mechanical distortion of the substrate, each micro-element comprising polysilsesquioxane; depositing a liquid media carrying the cells on the apparatus so that the cells settle on or adhere to the micro-elements; and releasing at least one selected micro-element having the cells thereon by application of gradual mechanical pushing energy to the second surface of the substrate opposite the well in which the at least one selected micro-element is disposed until the at least one selected micro-element is released; and then collecting the at least one selected micro-element.

In some embodiments of the method each micro-element of the plurality of micro-elements further comprises ferromagnetic particles. In other embodiments each micro-element of the plurality of micro-elements further comprise a silane coupling reagent having the general formula R—Si(R')$_3$, where R' can be one or more of OH, Cl or alkoxyl and where R has a terminal functional group comprising an epoxide, amine, carboxyl, vinyl, mercapto, or imine. The R-terminal functional group may in some embodiments be covalently bound to a biologically or chemically active moiety.

In another embodiment, the application of gradual mechanical pushing energy is carried out by positioning a probe adjacent the second surface of the substrate and oriented towards the at least one selected micro-element, and then progressively contacting the probe to the substrate until the at least one micro-element is released therefrom. A cell or cell colony may be isolated by the method.

A further aspect of the invention is a method of making an apparatus for collecting or culturing cells or cell colonies, the method of making comprising: providing a substrate formed from an elastomer and having a first surface and an opposed second surface and a plurality of wells formed in the first surface in the form of an array; coating the substrate with a fluid mixture comprising a polysilsesquioxane and a compatible solvent; drying the coated substrate for removing the solvent and forming a rigid low auto-fluorescent cell carrier in each of the wells. In one embodiment, the compatible solvent is gamma-butyrolactone (GBL).

In some embodiments, the method of making uses the elastomer polydimethylsiloxane. In other embodiments, the method of making further comprises a polysilsesquioxane and compatible solvent mixture that further comprises ferromagnetic particles. In some embodiments the polysilsesquioxane is a thermosetting polysilsesquioxane resin. In further embodiments the polysilsesquioxane resin is polymethylsilsesquioxane.

In some embodiments, the method of making further comprises cell carriers that are functionalized with a silane coupling reagent having the general formula R—Si(R')$_3$, where R' can be one or more of OH. Cl or alkoxyl and where R has a terminal functional group comprising an epoxide, amine, carboxyl, vinyl, mercapto, or imine. The functionalized micro-elements may further comprise a covalently bound biologically or chemically active moiety.

BRIEF DESCRIPTION OF THE DRAWINGS

For a more complete understanding of the present invention, reference should now be had to the embodiments shown in the accompanying drawings and described below. In the drawings:

FIG. 4A shows the preparation of a mixture of GR650F, a ferromagnetic nanoparticle, and GBL. Exchange of ligand from oleic acid to gallic acid made the nanoparticles stably dispersed in GBL.

FIG. 4B shows a photographic image of a mixture of GR650F, a ferromagnetic nanoparticle, and GBL in a glass vial wherein the mixture is pulled up against gravity in the vial using an external magnet.

FIGS. 6A-6D show images of single cell isolation and cloning enabled by a magnetic glass resin microraft array.

FIG. 6A shows images of a mixture of H1299 and GFP-H1299 cells on an array and a single GFP-H1299 cell (indicated by an arrow) identified. Top panel: brightfield image; bottom panel: fluorescence image using a FITC filter set.

FIG. 6B shows images of the GFP-H1299 cell identified in FIG. 6A isolated and transferred to one well of a 96-well plate. The well was filled with 150 μL medium containing 10 μg/mL human fibronectin, which coated the glass resin microraft and well and assisted the migration of cells from the glass resin microrafts to the well. Top panel: brightfield image; bottom panel: fluorescence image using a FITC filter set.

FIG. 6C shows images at 24 h after cell isolation. The single cell is divided into two cells. Top panel: brightfield image; bottom panel: fluorescence image using a FITC filter set.

FIG. 6D shows images at 72 h after cell isolation. The single cell is proliferated into a colony of GFP-H1299 cells. Top panel: brightfield image; bottom panel: fluorescence image using a FITC filter set.

FIG. 8A is a schematic drawing showing refractive indexes of microraft, PDMS, and cell culture medium. Image quality of GR650F microrafts can be improved due to refractive index homogeneity with surrounding medium and material.

FIG. 8B is a bright field image of HeLa cells cultured on magnetic polystyrene-based microrafts. Cells located near the edge of microrafts (indicated by arrows) were partially shaded by dark borders.

FIG. 8C is a brightfield image of H1299 cells cultured on magnetic GR650F microrafts. Scale bar=100 μm.

DETAILED DESCRIPTION

Figure 1:
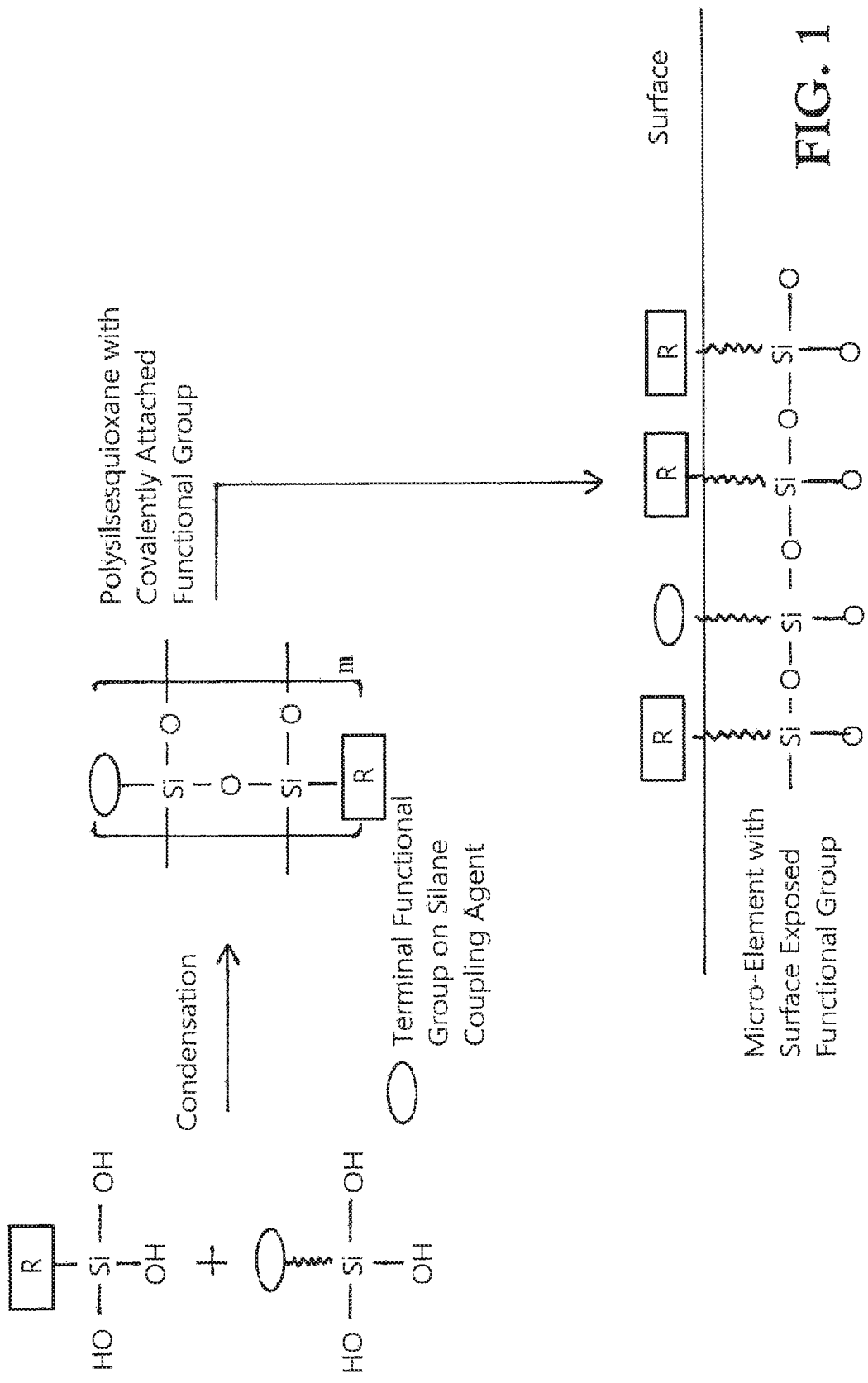
FIG. 1 shows co-polymerization of a polysilsesquioxane with a functionalizing reactive group and formation of a micro-element with surface exposed functional group.

An array of magnetic or paramagnetic microfabricated elements, or micro-elements, comprised of polymeric forms of silsesquioxane, or polysilsesquioxanes, is provided having ultra-low-autofluorescence and other optical and chemical properties to improve microscopic imaging and analysis of cells or other objects present on the array.

Polysilsesquioxanes are a family of high-performance, thermosetting resins based on an alternating silicon-oxygen network and fabricated using purified monomers that yield polymers having exceptional properties. The polysilsesquioxanes cure by condensation and, once cured, are insoluble in all common organic solvents. It has been discovered that polysilsesquioxanes can be used to make micro-elements with improved optical and imaging properties compared to polystyrene or other polymeric plastics typically used with cell isolation and culture. It has been further discovered that various polysilsesquioxanes can be used for the desired structural, functional properties for the fabrication of ferromagnetic micro-element arrays. Polysilsesquioxanes also enable the chemical modification of the micro-element surface for addition of functional biochemical or chemical moieties.

A silsesquioxane is an organosilicon compound with the chemical formula $[RSiO_{1.5}]_n$ (for example, R=alkyl, aryl or alkoxyl), where each silicon atom is bound to an average of one and a half (sesqui) oxygen atoms and to one hydrocarbon group (ane). Silsesquioxanes are colorless solids that adopt cage-like or polymeric structures with Si—O—Si linkages and tetrahedral Si vertices. Diverse substituents (R) can be attached to the Si centers. The molecules are unusual because they feature an inorganic silicate core and an organic exterior. The silica core confers rigidity and thermal stability. Silsesquioxanes are known in molecular form with 6, 8, 10, and 12 Si vertices, as well as polymers.

Silsesquioxanes are synthesized by using trifunctional organosilane compounds and are an organic/inorganic hybrid material that combines the inorganic characteristics presented by the siloxane bond (Si—O—Si), which constitutes the main chain, and the organic characteristics presented by the organic functional group that constitutes the side chain. Silsesquioxanes offer a flexibility in chemical design since the siloxane bond of the inorganic structure shows excellent transparency, heat resistance, hardness, and electrical resistance, and the organic functional group gives such functions as compatibility or dispersion stability, adjustment of fraction factor and permittivity, and reactivity (epoxy, acryl, etc.). Furthermore, it is known that polysilsesquioxanes can be produced having a random structure, a ladder structure, or a cage structure where each form shows different characteristics not only by changing the types of organic functional bases, but also the control of such structures, degree of polymerization, or the molecule end group. One example of such a polymer is polymethylsilsesquioxane. Polysilsesquioxanes may also be formed from polyhedral oligomeric silsesquioxanes ("POSS"), which have attracted attention as precursors to ceramic materials and nanocomposites.

These materials are amenable to being functionalized through chemical modification allowing surface attachment of affinity capture moieties or chemical reporters for selective binding or analysis of cells, macromolecules or other targets. Processes are described for manufacturing high resolution arrays including the formulation of micro-elements and micromolding of the individually-releasable, ferromagnetic micro-elements in an array format having improved optical properties, including ultra-low autofluorescence. The arrays produced using these processes and compositions overcome a number of problems related to image acquisition and analysis caused by the use of polystyrene in previous microraft arrays. Also, chemical modification of the micro-element material permits preferential attachment of affinity capture and chemical moieties to the microraft while excluding these modifications from the substrate where the micro-element resides in a well. Covalent attachment of functionalizing chemistries can be achieved at the time of manufacturing the micro-elements through co-polymerization or polymer capping methods, or alternatively by surface treatment of a micro-element immediately prior to a given experiment by the end user. The micro-elements and arrays containing them provide several benefits for research in the life sciences, among them are improved, high-resolution and high-content imaging of subcellular structures of live cells; isolating the target cells for clonal expansion or downstream molecular analysis based on phenotype analysis prior to collection from the array; and high-precision affinity-based capture of cells, macromolecules or other targets of interest.

Embodiments of the invention now will be described more fully with reference to the accompanying drawings, in which embodiments of the invention are shown. This invention may, however, be embodied in many different forms and should not be construed as limited to the embodiments set forth herein. Terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" or "comprising," when used in this specification, specify the presence of stated features, steps, operations, elements, or components, but do not preclude the presence or addition of one or more other features, steps, operations, elements, components, or groups thereof. Additionally, comparative, quantitative terms such as "above", "below", "less", "more", are intended to encompass the concept of equality, thus, "less" can mean not only "less" in the strictest mathematical sense, but also, "less than or equal to."

Unless otherwise defined, all terms (including technical and scientific terms) used herein have the same meaning as commonly understood by one of ordinary skill in the art to which this invention belongs. It will be further understood that terms used herein should be interpreted as having a meaning that is consistent with their meaning in the context of this specification, commonly used dictionaries, and the relevant art and will not be interpreted in an idealized or overly formal sense unless expressly so defined herein. Well-known functions or constructions may not be described in detail for brevity and/or clarity.

Like numbers refer to like elements throughout. In the figures, the thickness of certain lines, layers, components, elements or features may be exaggerated for clarity. Where used, broken lines illustrate optional features or operations unless specified otherwise.

As used herein, the term "and/or" includes any and all possible combinations or one or more of the associated listed items, as well as the lack of combinations when interpreted in the alternative ("or").

It will be understood that when an element is referred to as being "on," "attached" to, "connected" to, "coupled" with, "contacting," etc., another element, it can be directly on, attached to, connected to, coupled with and/or contacting the other element or intervening elements can also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature can have portions that overlap or underlie the adjacent feature.

Spatially relative terms, such as "under," "below," "lower," "over," "upper" and the like, may be used herein for ease of description to describe an element's or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus the exemplary term "under" can encompass both an orientation of over and under. The device may otherwise be oriented (rotated 90 degrees or at other orientations) and the spatially relative descriptors used herein interpreted accordingly. Similarly, the terms "upwardly," "downwardly," "vertical," "horizontal" and the like are used herein for the purpose of explanation only, unless specifically indicated otherwise.

It will be understood that, although the terms first, second, etc., may be used herein to describe various elements, components, regions, layers and/or sections, these elements, components, regions, layers and/or sections should not be limited by these terms. Rather, these terms are only used to distinguish one element, component, region, layer and/or section, from another element, component, region, layer and/or section. Thus, a first element, component, region, layer or section discussed herein could be termed a second element, component, region, layer or section without departing from the teachings of the invention. The sequence of operations (or steps) is not limited to the order presented in the claims or figures unless specifically indicated otherwise.

The micro-elements of the invention are arranged in an array that is generally comprised of a substrate formed from a flexible resilient polymeric material and having a plurality of wells formed therein. The micro-elements are releasably connected to the wells of the substrate, with said micro-elements arranged in the form of an array, and with each of the micro-elements resiliently received in one of said wells. The wells in said substrate can be separated by walls. The walls may be uniform or non-uniform and of any suitable dimension. In some embodiments, the walls have an average width of at least 2 micrometers, up to 5, 10, 100, 200, 500, or 1000 micrometers. In general, the walls have an average height of at least 2 or 5 micrometers, up to 200, 500, or 1000 micrometers. The wells in the substrate in some embodiments have floors. The floors can be uniform or non-uniform and of any suitable thickness. In some embodiments, the floors have an average thickness of from 2 or 5 to 200 or 500) micrometers.

"Substrate" as used herein is, in general, a flexible or elastomeric substrate, and may be conveniently formed from a material in which wells may be produced and the micro-elements formed directly therein. The wells are preferably made in a first surface of the substrate. Examples include, but are not limited to, silicones (e.g., polydimethylsiloxane (or "PDMS"), SILASTIC, TEXIN and CHRONOFLEX silicone materials), polyurethane substrates, styrene-butadiene copolymer, styrene-ethylene-butylene copolymer, polyolefin and polydiene elastomers, thermoplastic elastomers, other biomedical grade elastomers, etc. In one embodiment, the substrate can easily be fabricated by casting PDMS on a mold made by standard photolithography on a glass slide with a 40-100 µm thick SU-8. The microwell substrate may also be fabricated by hot embossing or thermoforming on a suitable mold, or by any other suitable technique, such as printing or microprinting. The array of micro-elements may be in any suitable uniform or non-uniform arrangement, including but not limited to interdigitated arrays and/or tilings. In one embodiment, the micro-elements are used as cell carriers to create arrays as described in U.S. Pat. No. 9,068,155, and US 2015/0210972, both of which are incorporated herein by reference in their entirety.

The micro-elements may be in any suitable geometry, including cylindrical, elliptical, triangular, rectangular, square, hexagonal, pentagonal, octagonal, concave, convex, etc., including combinations thereof. In some embodiments, the carriers have heights of at least 2 micrometers, up to 400 or 500 micrometers. In some embodiments, the carriers have maximum widths of at least 5 or 10 micrometers, up to 1000 micrometers. While any desired physical or structural feature can be incorporated into the carrier top portion, alone or in combination, in one embodiment a concave top surface portion is conveniently formed by meniscus coating of the side walls of said wells or cavities in the substrate during the process of casting said carriers in those cavities or wells. These micro-elements may be also variously referred to as micron-scale element, microrafts, rafts, cell rafts, cell carriers, carriers, and the like.

Any number of micro-elements may be contained in an array. In some embodiments an array may comprise as few as 10 micro-elements up to 500,000 micro-elements depending on the size of the micro-elements. The number of micro-elements in an array is limited only by the chosen dimensions of the substrate and the size of micro-elements used.

The micro-element arrays of the invention provide a method of collecting or culturing cells or cell colonies, generally involving the steps of: (a) providing an apparatus comprising a common substrate, the substrate formed from an elastomer and having a plurality of wells formed therein in a first surface in the form of an array, and a plurality of micro-elements releasably received in those wells, as described above; (b) depositing a liquid media carrying the cells (including but not limited to non-adherent cells) on apparatus so that the cells settle on or adhere to the micro-elements; and then (c) releasing at least one selected micro-element having the cells thereon by application of release energy to an opposing second surface of the substrate opposite each of the at least one micro-element from the well in which it is received. The released micro-elements may be collected by numerous suitable means and placed into tubes, multiwell plates, culture dishes, and the like for further analysis or culture.

Release energy may be applied as a burst of energy, or may be applied in a gradual manner. In some embodiments of the present invention release energy is applied gradually, for example, by gradual mechanical pushing or vibrating. In general, any suitable device for applying a release energy gradually may be employed. In some embodiments, mechanical pushing is carried out by positioning a probe (e.g., a blunt probe, a needle, micropipette tip, etc), adjacent (e.g. above, below) beneath the common substrate and oriented towards the at least one selected micro-element, and then progressively contacting the probe to the substrate. In some embodiments the probe does not pierce the substrate; in other embodiments the probe pierces the substrate and contacts and dislodges the at least one micro-element. In some embodiments the pushing is aided by or guided by a microscope (e.g., an optical microscope, a fluorescent microscope). In such embodiments, the probe may be connected to or mounted on the microscope objective in a configuration that permits visualization of the selected micro-element to be dislodged by the probe through the microscope objective as an aid or guide to carrying out the pushing or dislodgement of the selected micro-element. The microscope may be a simple manual optical microscope, with pushing carried out manually, or a partially or fully automated microscope with pushing or dislodgement of the micro-element achieved or carried out in an automated manner by movement of the objective (e.g., with a manual or automated XYZ drive stage, and/or with a drive or drive assembly included in the microscope objective assembly).

Micro-elements of the present invention may be composites of two or more (e.g., 2, 3, 4, 5, 6) layers, with each layer formed of a different material, or having a different composition, than the immediately adjacent layer or layers. This feature can be used to incorporate a variety of advantageous structural and/or functional features into the micro-element. In some embodiments, the micro-elements may be made magnetic or ferromagnetic by incorporating magnetic or ferromagnetic particles or nanoparticles into one or more layers of the micro-element, which allow the collection of the micro-elements to be facilitated by the use of magnetic wands or other magnetic transfer devices. In some embodiments, the micro-elements comprise two or more layers so long as the optical properties of the micro-elements are not substantially reduced. In addition a cell-growth compatible upper layer on which cells can be grown may be added, such as a gel layer (e.g., matrigel or hydrogel, containing growth factors, antibodies, or the like). For example, the cell growth-compatible upper layer may comprise a hydrogel (optionally containing live feeder cells to facilitate the growth of cells thereon, in any suitable amount, e.g., from 1, 5 or 10 to 100 or 1,000 cells per micro-element, such as murine embryonic fibroblasts), a biodegradable polymer, a biologically active material or biomolecule as described above, etc.

Micro-elements of the invention can be formed in the wells of a substrate by any suitable technique known in the art, such as dip-coating, drain-coating, spin-coating, or spray-coating. The micro-elements can likewise be formed in the wells of a substrate by casting the micro-elements in the cavities or wells formed during fabrication of the substrate.

Fabricating micro-element arrays using polysilsesquioxanes has several advantages with respect to optical properties, including comparable refractive index relative to substrate materials such as PDMS and low autofluorescence relative to previous polystyrene microrafts. These properties allow clear imaging of fluorescent signals and subcellular features with a significant reduction in "shadowing" around the perimeter of the micro-element allowing more of the microelement area to be used for imaging.

The selection of a suitable polysilsesquioxane for fabrication of a micro-element of the invention depends on several physical, chemical, and optical properties. The uncured polysilsesquioxane is preferably soluble in a solvent (e.g. gamma-butyrolactone, isopropanol, ethanol, etc.) at a certain concentration (e.g. in the range of 20-80 wt %) that does not cause swelling, dissolution, or deformation of the substrate during the fabrication of the micro-element in the wells of the substrate. The solvent compatibility of many substrates is well known in the art, and is also easily determined empirically. For example, it is known in the art that substrates formed from polydimethylsiloxane (PDMS) do not swell in the presence of polar solvents such as gamma-butyrolactone, isopropanol, ethanol, etc.

A suitable polysilsesquioxane is also preferably optically transparent when cured, and possesses improved optical clarity relative to polystyrene. The measurement of optical transparency or transmittance is well known in the art and can be determined by any suitable means. The relative optical clarity of a transparent material can be measured by assessing the impact of its introduction to the imaging path on the spatial resolution power of an imaging system, which is defined as the minimum distance between two objects below which the objects can no longer be differentiated as separate. For example, a relative optical clarity measurement can be performed by acquiring brightfield images of a negative 1951 United States Air Force resolution target (ThorLabs, Newton, NJ) using a suitable microscope and digital camera, both without and with a thickness of the optically transparent material overlaid onto the resolution target. Within the two images, the spatial resolution can be quantified by calculating the contrast ratio of image intensities between the bright lines and dark spaces for each of the sixty rulings within the target and defined as the line spacing corresponding to a contrast ratio of the square root of 2. A polysilsesquioxane suitable for use in the micro-elements of the invention should have a degradation in spatial resolution of preferably less 95%, more preferably less than 90%, and most preferably less than 80% of the degradation from polystyrene.

A suitable polysilsesquioxane should also form a micro-element that possesses low autofluorescence. Autofluorescence is that fluorescence exhibited by a material in the background. When a fluorescent cell or cells are present on a material with a high autofluorescence, there is a deterioration in the signal to noise ratio of the cell's fluorescent signal. A low signal to noise ratio can obscure the detection or measurement of the fluorescent signal from a target cell or its subcellular components. It is preferable that a polysilsesquioxane should form a micro-element that has low to negligible autofluorescence in the range of 350-700 nm, which coincides with the range of wavelengths of the most frequently used dyes (e.g. FITC, OREGON GREEN, ALEXA FLUOR 488, DAPI, CY3, CY5, TEXAS RED, GFP, RhodamineB, Hoescht 33342, ALEXA FLUOR 594, ALEXA FLUOR 647) for fluorescence imaging. Autofluorescence can be determined using epi-fluorescence imaging on a suitable microscope. Using consistent exposure times and gain settings (for example, 1 sec exposure, 2× gain), images of micro-elements can be acquired both with the fluorescence source on (autofluorescence image) and the fluorescence source off (dark image). Using these images, average gray values for each image can be measured using a standard software program such as ImageJ. Average gray values for the dark images are subtracted from the average gray values from the autofluorescence image to account for any stray light present and not a result of autofluorescence. These dark-subtracted values are a measure of relative fluorescence. This procedure can be used across the normal range of wavelengths using a set of selected fluorescent dyes such as GFP, DAPI, and CY3. Time course experiments can be conducted by using a fluorescent standard such as the Autofluorescence Plastic Slide from Chroma (Bellows Falls, VT) as a normalization standard. These slides possess a stable level of autofluorescence over time and can be used to normalize for drift in arc lamp intensity typically seen as arc lamp bulbs age. A consistent exposure time and gain setting can be used to acquire images of the autofluorescence slide prior to each time-based measurement. Average dark-subtracted gray values can be determined as described above from these normalization images, and the dark-subtracted average relative fluorescence measurements can be divided by the averaged normalization values to enable the comparison of analysis performed at different times. A polysilsesquioxane suitable for use in the micro-elements of the invention should exhibit an autofluorescence that is preferably less than 75%, or more preferably less than 50%, or most preferably less than 25% of that exhibited by polystyrene under standardized testing conditions.

A suitable polysilsesquioxane must also produce a micro-element that possesses a refractive index that is closely matched to the refractive index of the substrate material. The refractive index determines how much light is bent, or refracted, when entering a material and when light passes through multiple layers having disparate indices the signal intensity and image clarity can be reduced. Preferably, the refractive index of the polysilsesquioxane micro-element should be within 10% of the refractive index of the substrate material used for the array, more preferably within 5%, and most preferably within less than 1%. The measurement of refractive index is well known in the art and can be determined by any suitable means.

A suitable polysilsesquioxane preferably forms a micro-element that has poor adhesion with a substrate, such as PDMS, so that the micro-element can be released from the wells of the substrate. A suitable polysilsesquioxane preferably possesses, when cured, sufficient mechanical strength to withstand the energy of release from the well of the substrate using a release probe. Poor adhesion and sufficient mechanical strength can be readily determined empirically without undue experimentation. Preferably, 80%, more preferably 90%, and most preferably greater than 95% of the micro-elements should be released intact from the wells of the substrate within three or less release cycles without disturbing neighboring micro-elements in the array.

One example of a suitable polysilsesquioxane is the polymethylsilsesquioxane GR-650F $(RSiO_{1.5})_n$ from Techneglas, where R is a methyl group. While in no way limiting the range of polysilsesquioxanes suitable for the invention, Table 1 lists several other exemplary and commercially available polysilsesquioxanes suitable for use in fabricating micro-elements having improved optical and imaging properties.

TABLE 1

A selection of available polysilsesquioxanes suitable for fabricating micro-elements.

| | Product Name | | | | | | | | | | |
|---|---|---|---|---|---|---|---|---|---|---|---|
| | GR100F | GR150F | GR630L | GR630S | GR650F | GR651L | GR653L | GR653LPP | GR654L | GR908F | GR950F |
| Physical Form | Flake | Flake | Liquid | Liquid | Flake | Liquid | Liquid | Liquid | Liquid | Flake | Flake |
| Color | Colorless | Colorless | Colorless | Colorless | Colorless | Colorless | Colorless | Colorless | Colorless | Colorless | Colorless |
| % Solids | 100 | 100 | 60 | 100 | 100 | 35 | 30 | 30 | 40 | 100 | 100 |
| Solvent | — | — | Xylene | — | — | Ethanol-Butanol | Methanol-Butanol | Methanol-Butanol | Methanol-Butanol | — | — |
| Solubility | Polar & Aromatic | Polar & Aromatic | Aromatics | — | Polar | Polar | Polar | Polar | Polar | Polar & Aromatic | Polar & Aromatic |
| Viscosity** | 20 | 17 | 24 | 550 | 28 | 11 | 11 | 11 | 12 | 15 | 14 |
| Specific Gravity | 1.3 | 1.3 | 1.05 | 1.16 | 1.3 | 1.3 | 1.3 | 1.3 | 1.3 | 1.3 | 1.3 |
| Refractive Index | 1.49 | 1.51 | 1.48 | 1.47 | 1.42 | 1.42 | 1.42 | 1.42 | 1.42 | 1.55 | 1.56 |
| Organics | Methyl-Phenyl | Methyl-Phenyl | Methyl-Phenyl | Methyl-Phenyl | Methyl | Methyl | Methyl | Methyl | Methyl | Methyl-Phenyl | Phenyl |

*Data source: http://www.techneglas.com/products/resins800.htm
**As supplied or 40% in Butanol, unit: cps.

In one embodiment, GR650F was used to make ultra-low-autofluorescence ferromagnetic micro-elements for use in an array made from the elastomeric polymer PDMS as substrate. In order to fabricate microrafts from GR650F a dip coating solution was first formulated comprising GR650F, ferromagnetic nanoparticles, and gamma-butyrolactone (GBL). Fabrication of the polysilsesquioxane micro-elements can be accomplished in various ways, for example using a dip-coating process similar to that used for fabricating microrafts from polystyrene.

The use of a suitable polysilsesquioxane to fabricate micro-elements should also allow for the incorporation of functional chemical or biochemical moieties. Polystyrene is difficult to chemically modify to allow both covalent and non-covalent attachment of functional moieties to the surface of the polymer. Replacing polystyrene with polysilsesquioxanes as the material composition of a micro-element allows the use of a more straightforward chemical modification method for subsequent attachment of biological or chemically active moieties.

In some embodiments, the invention includes the functionalization of the micro-elements by incorporating one or more biologically or chemically active moieties that provide, for example, affinity capture or reporters that react to the presence of a target chemical. Examples of such moieties include, but are not limited to, a peptide, a protein, a carbohydrate, a nucleic acid, aptamers, a lipid, a polysaccharide, a hormone, an extracellular matrix molecule, a cell adhesion molecule, a natural polymer, an enzyme, an antibody, an antigen, a polynucleotide, a growth factor, a synthetic polymer, polylysine, a small molecule such as a drug or other chemical, etc., including combinations thereof. Incorporation of the functional moieties is preferably through, but not limited to, covalent bonding. More particular examples of biologically active molecules include, but are not limited to, fibronectin, laminin, thrombospondin, collagen including collagen IV, elastin, tenascin, vitronectin, carbohydrates, and lipids, fibrinogen, tenascin, bovine pituitary extract, epidermal growth factor, hepatocyte growth factor, keratinocyte growth factor, and hydrocortisone. Also useful for functionalization of the micro-elements are pharmaceutical preparations or compounds: substances which influence the properties of biological cells; messengers; growth factors (e.g., vascular endothelial growth factor, bone morphogenic factor beta, epidermal growth factor, endothelial growth factor, platelet-derived growth factor, neural growth factor, fibroblast growth factor, insulin growth factor, or transforming growth factor); differentiation factors (e.g., neurotrophin, colony stimulating factor, transforming growth factor); antigens; allergens; etc. In some embodiments, fluorescent reporters such as fluorescent proteins that change their fluorescence intensity or color in response to a biochemical or biophysical change (e.g. fluorescent gelatin for invadopodia assay) and synthesis substrates for enzymes coupled to fluorophores, fluorescence quenchers, or chemical reporters such as sensor dyes that detect oxygen, pH, reactive oxygen species (ROS), nitric oxide, etc., and chemiluminescent enzymes such as luciferase, can be bound to the microelement.

In one embodiment, the micro-element can incorporate different types of biological reagents (for example, drugs, antibodies, growth factors, DNA plasmid, fluorescent reporters, etc.). These reagents can be covalently attached to the micro-elements through one or more functional groups exposed on the surface of the micro-element. Cells can then be plated on the array and the cell-reagent interactions can be quickly screened. The cells with desirable interactions can be released from the array and collected for further study. A very large number of rafts can be created on the array, e.g. 1 inch×1 inch array contains 45,000 rafts (100 μm size). Many types of reagents or many different mixing ratios can be attached to the array; therefore, the functionalized micro-element array provides a platform for studying cell-reagent interaction.

In another embodiment, a biologically or chemically active moiety is bound only to the micro-element itself while being entirely excluded from binding to the walls of the substrate surrounding the micro-element. This property is particularly useful when, for example, the bound moiety is an affinity capture tag. Otherwise, targets intended to be captured on the micro-element (i.e. cells) will be attached to the microwell walls, rendering them largely unobtainable for downstream analysis through the release of the micro-element. Thus, the micro-elements of the invention allow for the selective binding of biological or chemical moieties independent of the chemical properties of the substrate material.

The core structure of the silsesquioxane monomer features three silanol groups (FIG. 1). This structure has broad capabilities for functionalization including the incorporation of epoxides, amines, carboxyls, alkenyls such as vinyl, mercapto, imides and other functional groups. Each of these chemical modifications can be used in a second reaction to covalently attach one or more biologically or chemically active moieties as well as affinity capture moieties comprising antibodies, peptides or aptamers. Various silane compounds are commercially available for use in introducing reactive groups into the polysilsesquioxane structure in order to functionalize the micro-elements. Exemplary sources of such compounds are Gelest, Inc. (Morrisville, PA) and Sigma-Aldrich (St. Louis, MO).

Figure 2:
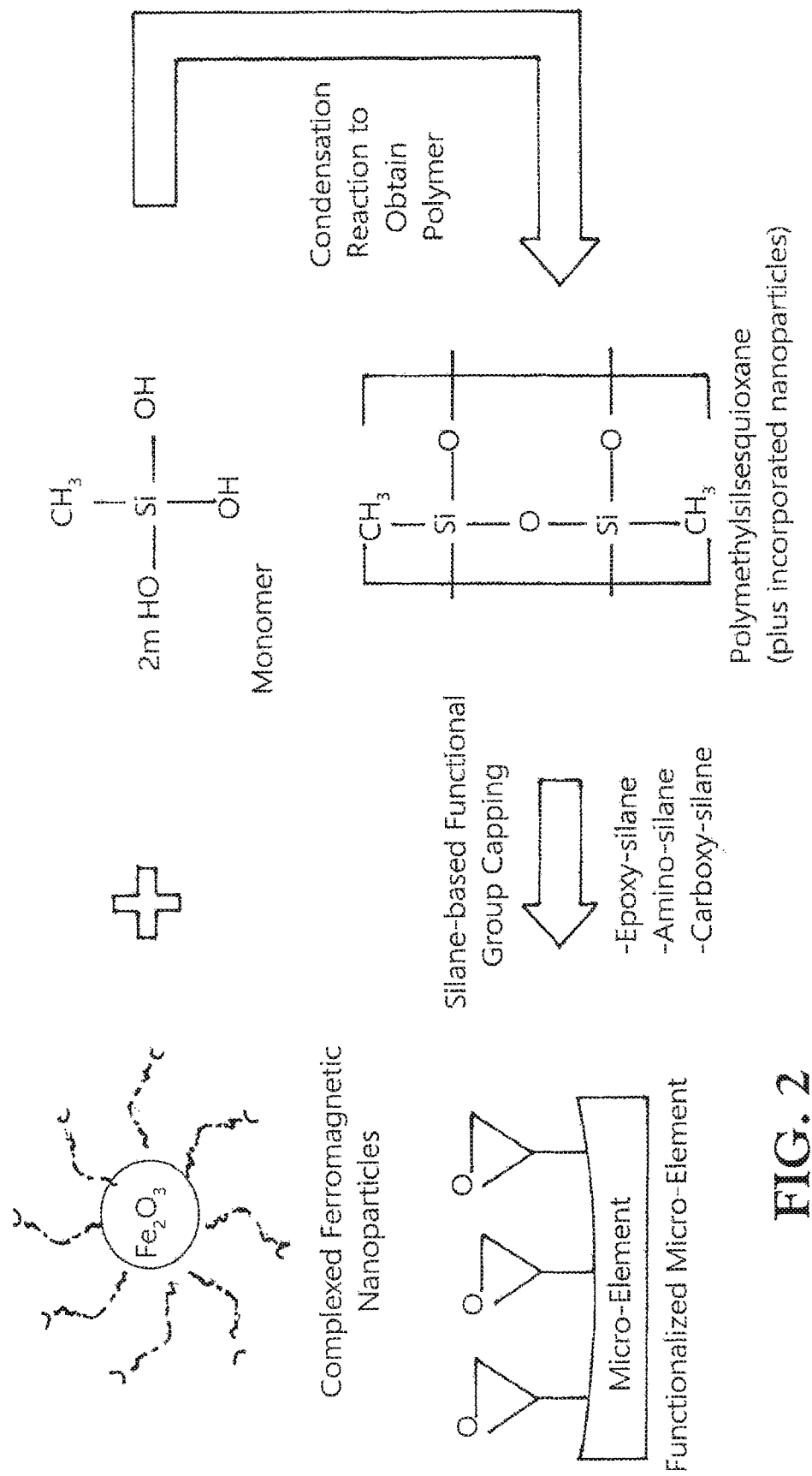
FIG. 2 shows preparation of epoxide functionalized polysilsesquioxane including the use of ferromagnetic particles which is optional.

Suitable silane coupling reagents useful for incorporation into the micro-element for purposes of functionalization have the general formula R—Si(R')$_3$, where R' can be one or more of OH, Cl or alkoxyl and where R has a terminal functional group comprising an epoxide, amine, carboxyl, vinyl, mercapto, or imine. (FIG. 1, where R=OH). R—Si(OH)$_3$ is a reactive silane compounds which can be hydrolyzed from a stable silane compound R—Si(R")$_3$ where R" is chlorine, methoxyl, or ethoxyl. Condensation and/or co-polymerization reactions with the polysilsesquioxanes during formation of the micro-element introduces the functionalizing silane into the polymer structure as siloxane linkages (see FIG. 1). The use of compounds having the silane functional group can also be used in a "capping" reaction after the polysilsesquioxane is condensed to a polymer. An exemplary fabrication process is shown in FIG. 2. Exemplary silane coupling agents are 3-glycidoxypropyl methyl-dimethoxysilane (epoxide functional group), vinyltrimethoxysilane (vinyl functional group), 3-aminopropyltriethoxysilane (amine functional group), 3-mercaptopropylmethyldimethoxysilane (mercapto functional group), 3-triethoxysilyl)propylsuccinic anhydride (carboxyl functional group upon hydrolysis of anhydride), and triethoxysilylpropylmaleamic acid (carboxyl function group). Residual silanol (SiOH) groups at the surface of polysilsesquioxane can be capped with a silane compound R(SiR$_1$)$_3$ where R$_1$ is chlorine, hydroxyl, methoxyl, or ethoxyl. Examples of the silane compounds are glycidoxy-propyltrimethyoxysilane, aminopropyltriethoxysilane, vinyltrichlorosilane.

Figure 3:
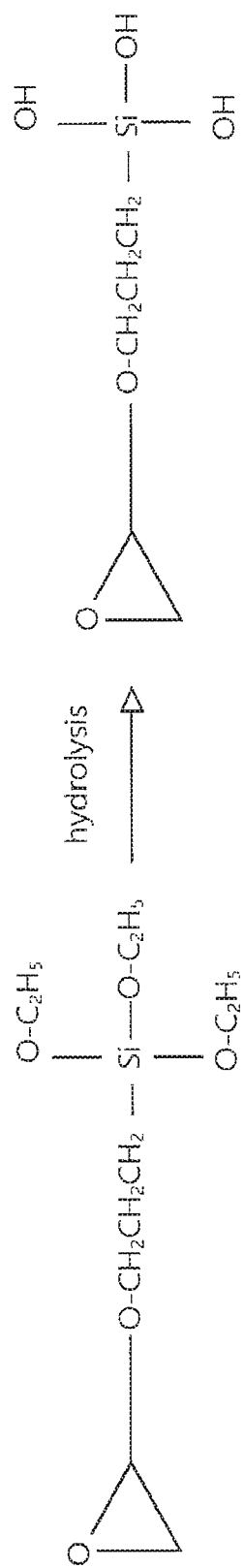
FIG. 3 shows hydrolysis of glycidoxy-propyltrimethyoxysilane (GOPTS) resulting in replacement of the methyoxyl groups with silanol groups, allowing copolymerization with unmodified GR650F and exposed epoxide groups on the polymer surface.

In one embodiment, epoxide groups can be added to the core structure of the polysilsesquioxane GR650, which can then be used for the covalent attachment of affinity tags. To generate the epoxide-modified polysilsesquioxane a trimethyoxysilane compound, 3-glycidoxy-propyltrimethyoxysilane (or GOPTS) can be used. Hydrolysis of GOPTS results in replacement of the methyoxyl groups around the central silicon with hydroxyl groups compatible with GR650F polymerization (FIG. 3). GOPTS has been used in other materials, such as glass, for chemical surface functionalization. Typically, GOPTS is a silane coupling reagent and is applied to a hydrophilic, hydroxyl group containing surface (e.g. glass, or plasma treated plastics/elastomers) to produce surface epoxide groups.

EXAMPLES

Example 1: Formulation of Stably Dispersed Ferromagnetic Nanoparticles in a Mixture of GR650F and Gamma-Butyrolactone (GBL)

In one embodiment, ferromagnetic nanoparticles were capped with oleic acid to allow the nanoparticles to be stably dispersed in a non-polar solvent such as toluene. The long aliphatic chain of oleic acid is used to prevent the aggregation of nanoparticles. Toluene, however, is not compatible with the silicone polymer PDMS typically used for the array substrate and causes swelling of the PDMS. An aprotic polar solvent, gamma-butyrolactone (GBL), was previously discovered not to cause swelling of PDMS but in which polymers such as polystyrene are soluble, making it a suitable solvent for the fabrication of polystyrene-based microrafts. Using GBL as the solvent, however, resulted in rapid aggregation of the ferromagnetic nanoparticles in the GBL. To reduce or eliminate this aggregation a small moiety of acrylic acid, 1.5%, was added to the polystyrene chain. During the formulation process it is expected that the oleic acid moiety is replaced by the acrylic acid moiety during the exchange of solvent from toluene to GBL. This ligand exchange helps to stabilize the ferromagnetic nanoparticles in GBL. When using polystyrene in combination with ferromagnetic nanoparticles prepared as above in GBL as solvent the composition is stable for long periods without aggregation of nanoparticles.

Fabrication of micro-elements using polysilsesquioxanes presented a challenge because the polysilsesquioxane does not contain carboxyl groups that allow ligand exchange with oleic acid present on the ferromagnetic nanoparticles. When the polysilsesquioxane GR650F was combined with ferromagnetic nanoparticles in toluene and GBL, the ferromagnetic nanoparticles instantaneously aggregated. To address this challenge, it was discovered that capping the nanoparticles with a polar molecule such as gallic acid through ligand exchange allowed the nanoparticles to be stably dispersed in GBL. FIG. 4A shows the ligand exchange of oleic acid-capped ferromagnetic nanoparticles with gallic acid. After the ligand exchange, ferromagnetic nanoparticles were capped with gallic acid instead of oleic acid.

In order to fabricate micro-elements using polysilsesquioxanes, oleic acid-capped ferromagnetic nanoparticles stably dispersed in toluene was prepared. To exchange the ligand, 2 g gallic acid was dissolved in 10 mL GBL, followed by adding 10 mL ferromagnetic nanoparticle (2.5 wt %) solution in toluene and then 30 mL ethanol. The mixture was stirred for 10 min. The mixture was then placed on a rotary evaporator at 70° C. for 30 min to remove toluene and ethanol, resulting in a darkly colored solution. To remove oleic acid and excess gallic acid, 60 mL hexane/ethanol (50:50 vol:vol) was mixed with the above solution, and centrifuged at 7,000 rpm for 5 min to precipitate the nanoparticles. The supernatant was decanted. The gallic acid-capped nanoparticles were dispersed in 10 mL GBL, and rinsed with 60 mL hexane/ethanol (50:50 vol:vol) and centrifuged at 7,000 rpm for 5 min. The rinse was repeated three times to ensure the complete removal of oleic acid and excess gallic acid. Finally the nanoparticles were dispersed in 10 mL GBL to generate a darkly colored, stable solution.

In the second step, 10 g GR-650F polysilsesquioxane (Techneglas, Perrysburg, OH) was added to 10 mL nanoparticle/GBL solution. The GR-650F completely dissolved after an overnight period. The mixture was centrifuged at 7,000 rpm for 30 min to precipitate nanoparticle aggregates. Only a trace amount of aggregates was observed after centrifugation. The solution was then decanted to a glass vial. The composition of the mixture is GR650F:ferromagnetic nanoparticle:GBL=50:2.5:50 wt:wt:wt. The nanoparticles were stably dispersed and the solution was darkly colored. No precipitation or aggregation was observed over 3 months. The liquid composition could be magnetized and pulled up against gravity by a permanent magnet (FIG. 4B).

Figures 5A, 5B, 5C:
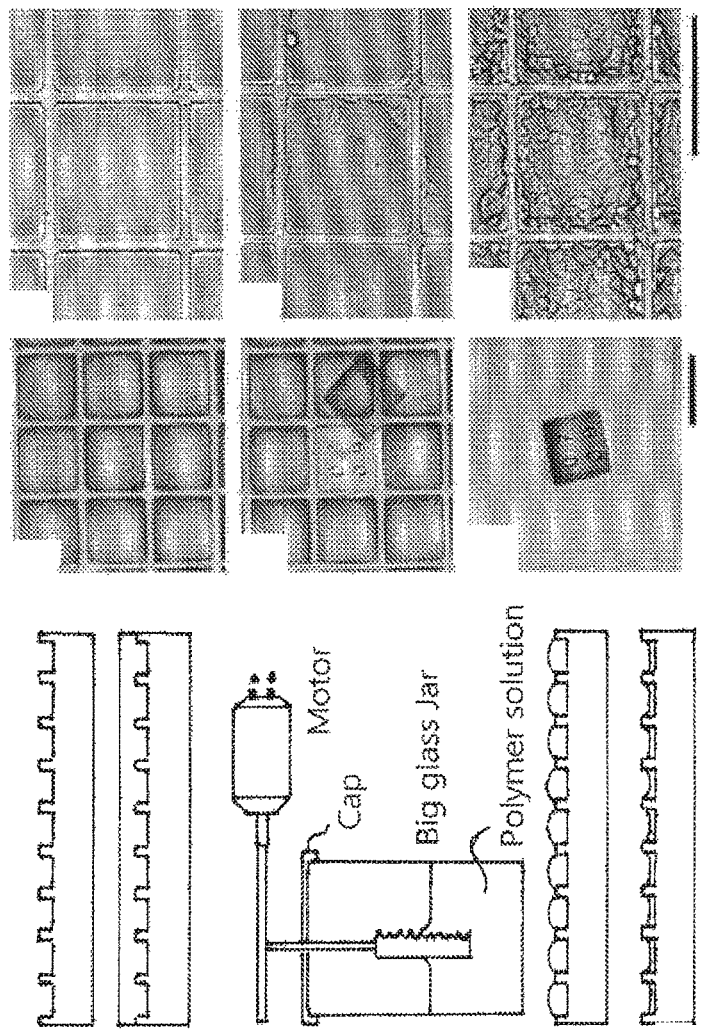
FIG. 5A shows a schematic drawing of an embodiment of a dip coating process for fabricating GR650F rafts on a PDMS microwell plate. The top panel shows a PDMS microwell template. In the panel directly underneath the top panel, a solution of GR650F ferromagnetic nanoparticles is added to the microwell array and subsequent degassing is used to remove trapped air bubbles. In the middle panel, the wetted template is immersed in the GR650F solution and then slowly withdrawn. The panel second from the bottom shows that dewetting of solution from the template results in retention of isolated convex GR650F solution in each well. The bottom panel shows that evaporation of solvent results in concave microrafts inside each well.
FIG. 5B shows photographic images of the selective release of a targeted microraft from the array by a needle. The top panel shows the array before release. The middle panel shows a targeted microraft labeled with a four-digit number (0709) released from the array leaving an empty microwell. The bottom panel shows the released microraft collected in a separate plate.
FIG. 5C shows images of culture on GR650F microrafts wherein HeLa cells proliferate on the microrafts at (top) 1 h, (middle) day 3 and (bottom) day 7. Scale bar=200 μm.

Example 2: Fabrication of Ferromagnetic GR650F Polysilsesquioxane Microraft Array Microrafts were fabricated from the above mixture (GR650F, ferromagnetic nanoparticle and GBL) by a dip coating process which utilizes discontinuous dewetting phenomena (FIG. 5A). A PDMS substrate containing microwell structures in an array was first fabricated by replica molding (FIG. 5A, top panel). The polysilsesquioxane composition was then added to the PDMS substrate in which microwells were formed (FIG. 5A, panel second from top). Degassing by vacuum was used if air bubbles were trapped in the microwells. Generating isolated microrafts inside individual microwells requires the polysilsesquioxane coating solution to be drained from the rigid plate surface by gravity without leaving any residue. Therefore, the coating solution must dewet from the PDMS substrate, which requires that the difference in the surface energy of the PDMS template and microraft solution be sufficiently large to ensure the discontinuous dewetting. This was satisfied in the current formulation by using GBL as the solvent, whose surface tension (35.4 dyne/cm) is different from that of PDMS (21 dyne/cm). An additional benefit of using GBL is that it is a solvent that does not swell PDMS. The microwell array was then immersed and withdrawn from the solution (FIG. 5A, middle panel). The withdrawal was performed at a constant speed controlled by a slow DC rotary motor so that the solution was allowed enough time to drain from the PDMS surface. To maintain a constant concentration, the dip-coating was performed in a sealed glass jar to prevent evaporation of GBL. After the entire plate was withdrawn from the solution, each microwell was observed to be filled with liquid possessing a convex surface (FIG. 5A, panel second from bottom). The array was then baked in a horizontal position at 95° C. for 16 h to evaporate the solvent. Evaporation resulted in shrinkage of the GR650F polymer and formation of a solid microraft with a concave surface (FIG. 5A, bottom panel). The thickness of this structure could be adjusted by altering the concentration of GR650F in the solvent. For example, by using 50 wt % concentration the height of the microraft was approximately ½ of the depth of the well. The dip-coating strategy permits very large arrays to be created with ease. As an example, an extended array of 300 mm×50 mm×0.2 mm containing >$10^6$ microrafts (100 µm square, 20 µm inter-microraft spacing) could be readily processed by this dip-coating method. The process provides for a simple mass production capability to create inexpensively high quality arrays containing polysilsesquioxane microrafts.

Example 3: Optimization of GR-650F Magnetic Solution Synthesis

The dispersion of ferromagnetic nanoparticles in a mixture of GR650F and GBL was modified to allow for a greater quantity of nanoparticles remaining dispersed for longer periods of time.

The first ligand exchange reaction involved adding 2 g gallic acid to 10 g of 200-proof ethanol and vortexing for 1 minute to fully dissolve the gallic acid. A 10 g quantity of nanoparticle solution (2.5% in toluene) was added to the dissolved gallic acid mixture and vortexed for 1 minute to mix. A 10 g quantity of GBL was then added, again followed by vortexing for 1 minute to mix. This mixture was then added to a 500-mL evaporating flask and rotary evaporated at 70° C. for 30 minutes to remove toluene and ethanol.

After rotary evaporation, a pre-mixed solution containing 20 mL of 200-proof ethanol and 15 mL of hexane was added to the 500-mL rotary evaporating flask containing the remaining GBL solution. The resulting solution was mixed thoroughly and decanted to a 50-mL conical vial. The conical vial was then placed next to a 2"×2"×4" N48 neodymium magnet for 15 minutes to magnetically decant the nanoparticles from the solution. Once the nanoparticles had condensed to the side of the tube near the magnet, the remaining liquid was poured from the tube while the magnet was held in place to remove excess gallic acid.

After the first liquid decanting, a pre-mixed solution containing 15 mL of 200-proof ethanol and 7.5 mL of hexane was added to the remaining nanoparticles. This mixture was shaken manually for 1 minute to resuspend the nanoparticles, then placed next to the magnet to decant the nanoparticles and further remove excess gallic acid. Once the nanoparticles separated from the solution (60 min to overnight), the liquid was again removed and this process was repeated one additional time for a total of three magnetic decanting steps.

After the final decanting step, 10 mL of GBL was added to the remaining nanoparticles and vortexed for 1 minute to mix. This mixture was then added to a 500-mL evaporating flask and rotary evaporated at 70° C. for 30 minutes to remove any remaining ethanol and hexane. After rotary evaporation, the mixture was cooled in an ice bath for 30 min.

Finally, 10 g of GR650F resin was added to the cooled nanoparticles in GBL mixture and was placed on a bottle roller for 3 hours to fully dissolve the resin. After dissolution, an optional overnight magnetic decanting could be performed to remove any unincorporated nanoparticles. This protocol produced ~15-18 mL of magnetic GR650F solution.

This procedure could be scaled up to produce the larger quantities of the GR650F magnetic solution for commercial fabrication. To demonstrate the ability to produce larger volumes of the material, a 2× reaction was performed by doubling the reagent quantities used in the optimized procedure above. The necessary mixing and decanting times required during the synthesis process remained the same, however the GR650F resin was mixed with the final nanoparticle solution in GBL for 16 hours to ensure full dissolution. This procedure resulted in ~35 mL of magnetic GR650F solution.

Example 4: Selective Release and GR650F Polysilsesquioxane Microrafts by a Needle Probe GR650F microrafts can be selectively detached from the PDMS microwell template by a stainless steel pin with tip diameter of 0.0125 mm and a base diameter of 0.1 mm (Fine Science Tools, #26002-10) (FIG. 5B). The microraft array was treated with plasma for 5 min to render a hydrophilic surface, and 2 mL Dulbecco's Modified Eagle Medium (DMEM) containing 10% fetal bovine serum (FBS) was added to the array. To test the release and collection efficiency, the polysilsesquioxane microrafts were released from the array using the steel pin by inserting the pin through the PDMS substrate under the microraft using a motorized CELLRAFT release device (Cell Microsystems, Inc., Research Triangle Park, North Carolina), and the released polysilsesquioxane microrafts were collected by attraction to a magnetic wand and transferred to a 96-well plate. All polysilsesquioxane microrafts (n=100) were successfully detached from the PDMS array substrate and collected by a magnetic wand. In terms of release efficiency, 66% microrafts were released in one attempt, 15% microrafts required two attempts, 12% microrafts required three attempts, and 7% microrafts required more than three pin insertions. All of the released polysilsesquioxane microrafts were collected by the magnetic wand and transferred to separated wells in a 96-well plate (i.e. collection and transfer efficiency=100%).

Example 5: Cell Culture on GR650F Polysilsesquioxane Microraft Array

Since the microrafts are the sites in intimate contact with cells, the polysilsesquioxane microrafts must support the attachment and proliferation of adherent cells. Plasma treatment is a standard surface modification process to introduce charged chemical moieties on cell culture devices such as polystyrene Petri dishes. GR650F polysilsesquioxane microraft arrays were treated with plasma for 5 min to render a hydrophilic surface, followed by 30 min sterilization by ultraviolet germicidal irradiation. The polysilsesquioxane microrafts were then coated with fibronectin (MILLIPORE FC010) overnight at 37° C. at 6.2 μg/cm$^2$ (i.e. 2 mL of 20 μg/mL fibronectin in PBS), followed by washing with 2 mL PBS buffer ×3 times. HeLa cells were plated on the microraft array at a cell density of 4,000 per array (12,000 microrafts per array). The distribution of cells on the array follows a Poisson distribution. At this cell density (cell:microraft=1:3), theoretical calculation shows that 72% of microrafts are empty, 24% microrafts have single cells, and 4% microrafts have ≥2 cells. Therefore, the majority of cells (>72%) are present as a single cell on a microraft. This distribution is important as it maximizes the number of sites with single cells, which then can form clonal colonies or be released and collected for single-cell analysis by PCR or other techniques.

HeLa cells attached to fibronectin-coated GR650F polysilsesquioxane microrafts in 2 h (FIG. 5C, top panel) as evidenced by their spreading morphology on the microrafts. The cells proliferated on the array over time (FIG. 5C, middle panel), and at day 7 the cells covered entire polysilsesquioxane microrafts (FIG. 5C, bottom panel). This result demonstrates that GR650F polysilsesquioxane microrafts are biocompatible and can support long-term culture of adherent cells.

Example 6: Single Cell Isolation and Cloning Capabilities Enabled by Arrays Containing Magnetic Polysilsesquioxane Microrafts To demonstrate the single cell isolation and cloning functions, a mixture of wild type H1299 (human non-small cell lung carcinoma cell line) and GFP-H1299 (stable transfection of green fluorescent protein [GFP]) cells were plated on an array composed of polysilsesquioxane microrafts at a ratio of 95:5 (H1299:GFP-H1299). At 4 hours after cell plating, single GFP-H1299 cells were identified on the array (FIG. 6A), isolated and transferred to a 96-well plate (FIG. 6B). The isolated single cells proliferated into a high purity colony (FIGS. 6C and 6D). Isolation efficiency was 100±0% (n=3 experimental replicates, 10 single cells isolated per experiment). Cloning efficiency of single cells was 93.3±5.8%, and 100±0% purity was obtained.

Example 7: Ultra-Low Autofluorescence of GR650F Polysilsesquioxane Microrafts Enabled High-Resolution Fluorescence Imaging of Subcellular Structures Fluorescence-based assays are important tools for cell selection. The fabrication of microrafts using polysilsesquioxanes rather than polystyrene was found useful in producing microrafts that exhibit lowered native fluorescence (autofluorescence). To measure native fluorescence, GR650F polysilsesquioxane microrafts were fabricated and compared to polystyrene-based microrafts and to No. 1 cover glass. Each were soaked in PBS buffer. The native fluorescence of the GR650F polysilsesquioxane microrafts, polystyrene microrafts, and No. 1 cover glass was examined using a NIKON ECLIPSE TE300 inverted epifluorescence microscope equipped with four fluorescent filter sets: a DAPI filter set (UV-2E/C; Nikon Instruments; excitation filter 340-380 nm, dichroic 400 nm long pass, emission 435-485 nm dichroic 500 nm long pass, emission 520 nm long pass); a fluorescein filter set (B-2A; Nikon Instruments; excitation filter 450-490 nm, dichroic 500 nm long pass, emission 520 nm long pass); a CY3 filter set (G-2E; Nikon Instruments; excitation filter 528-553 nm dichroic 565 nm long pass, emission 590-650 nm); and a Cy5 filter set (41008; Chroma Technology, Rockingham, VT; excitation filter 590-650 nm, dichroic 660-nm long pass, emission 665-740 nm). Images were collected with a cooled CCD camera (PHOTOMETRIX COOL SNAP; Roper Scientific, Tucson, AZ) using NIS-Elements software. The fluorescence intensity of individual microrafts was obtained from the fluorescence images using NIS-Elements software (Nikon Instruments).

Figure 7A:
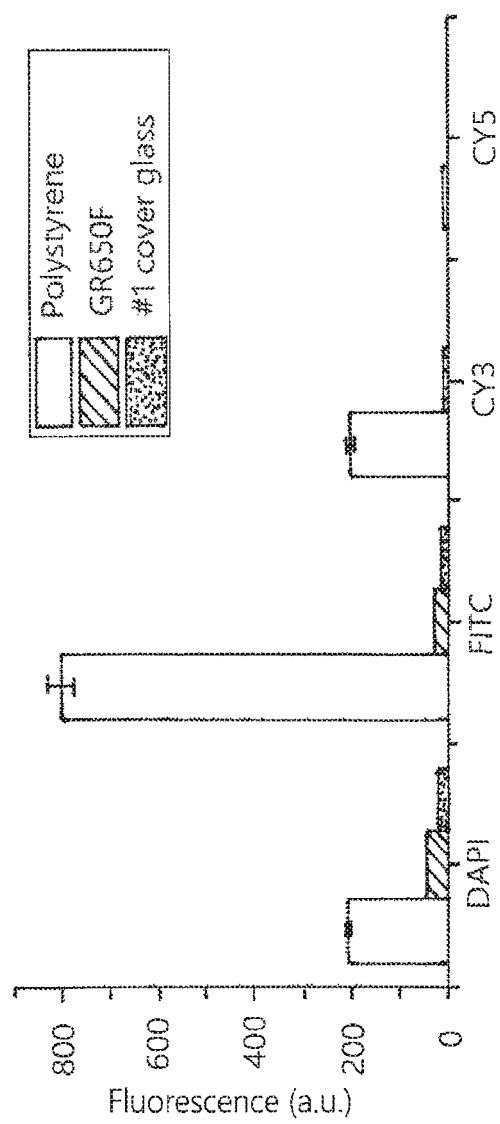
FIG. 7A is a graph of the autofluorescence of GR650F microrafts. Fluorescence intensity of the rafts is measured using four filter sets: DAPI, fluorescein, CY3 and CY5.

Using a DAPI filter set, the fluorescence of GR650F polysilsesquioxane microrafts was only 21% that of polystyrene-based microrafts (FIG. 7A). Using a fluorescein filter set, the fluorescence of GR650F polysilsesquioxane microrafts was only 3.4% that of polystyrene-based microrafts. Using a CY3 filter set, the fluorescence of GR650F polysilsesquioxane microrafts was only 3.6% that of polystyrene-based microrafts. Using a CY5 filter set, the fluorescence of GR650F polysilsesquioxane microrafts was only 16% that of polystyrene-based microrafts. At shorter wavelengths, the fluorescence of GR650F polysilsesquioxane microrafts were only slightly higher than No. 1 cover glass, a standard material for high-resolution fluorescence imaging. This is probably due to the PDMS substrate (about 200 μm thickness) underneath the GR650F polysilsesquioxane microrafts.

These data demonstrated that GR650F microrafts have much lower autofluorescence than polystyrene-based microrafts and thus should enable high-resolution fluorescence imaging of subcellular structures. To demonstrate this capability, HeLa cells were cultured on the polystyrene-based and GR650F polysilsesquioxane microrafts for 4 hours. The mitochondria were stained with 250 nM MITOTRACKER Red CMXRos (ThermoFisher Scientific, M-7512) for 20 min. The cells were then fixed with 4% paraformaldehyde for 15 min, and permeabilized with 0.2% Triton X-100 in PBS for 10 min. The actin filaments of the cells were stained with ACTINGREEN 488 READY-PROBES Reagent (ThermoFisher Scientific, R37110) for 5 min at a diluted concentration of 10 μL reagent per 1 mL PBS. Finally, the nuclei of the cells were stained with Hoechst 33342 (2 μg/mL in PBS) for 15 min.

Figure 7B:
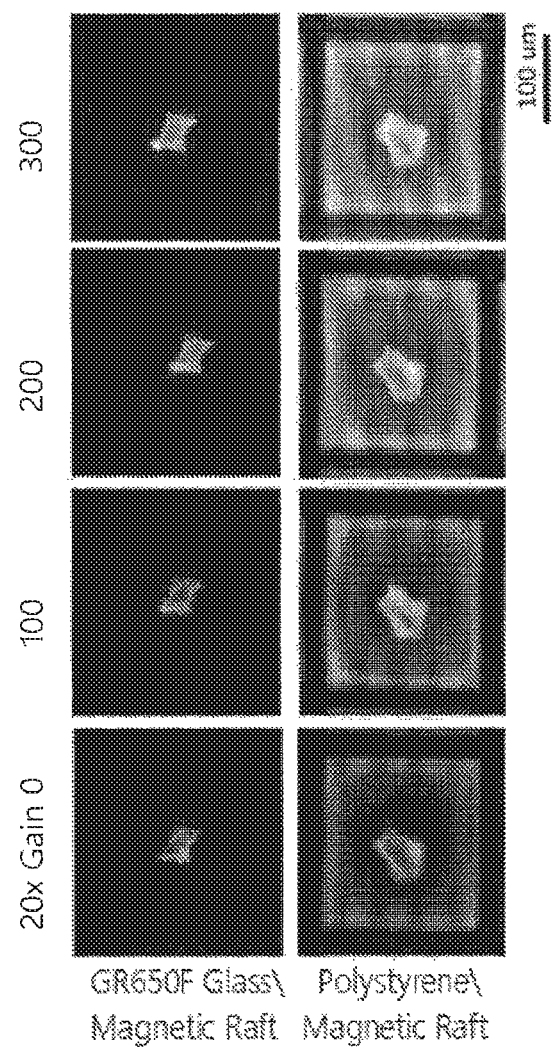
FIG. 7B is a series of images of the autofluorescence signals of the GR650F microrafts. The autofluorescence signals are reduced in the GR650F rafts compared with polystyrene rafts, the GR650F raft arrays enabling the use of higher gain when cells are seeded on the array due to the reduction in autofluorescence.

FIG. 7B shows the cells imaged using a 20× objective under the fluorescein filter set at various gain levels. Compared with polystyrene-based microrafts, GR650F polysilsesquioxane microrafts exhibited both reduced autofluorescence and improved imaging properties by permitting higher gain settings and providing higher resolution during cell imaging.

Figure 7C:
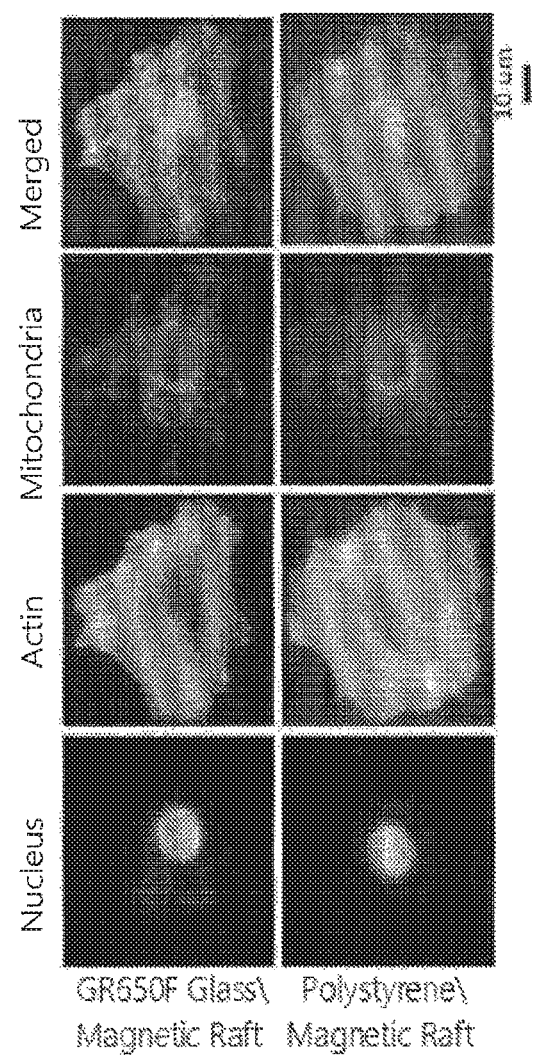
FIG. 7C is a series of images showing GR650F rafts enabling higher resolution imaging of HeLa cells, allowing improved abilities to visualize subcellular features of actin filaments and mitochondria.

FIG. 7C shows a high-resolution image of a HeLa cell on a GR650F polysilsesquioxane microraft (top panel) using a 60× objective. Subcellular structures (mitochondria and actin filaments) were clearly revealed. As a comparison, subcellular features of cells on polystyrene-based microrafts (bottom panel) were poorly revealed or unresolved under the same conditions.

Example 8: Improved Image Quality by Reducing or Eliminating Inhomogeneity of Refractive Index Across Array Components When cells are imaged on a microraft array the microraft comes in direct contact with medium and the array substrate. The component materials of the array, however, possess different refractive indices (FIG. 8A). For example, a polystyrene-based microraft (refractive index n=1.592) has a markedly different refractive index compared with PDMS (n=1.41) and cell culture medium (n=1.35). The inhomogeneity of refractive indices affects the image quality of the cells on the array, for example, by causing a dark border along the edge of each polystyrene-based microraft when the microraft array is imaged under brightfield (FIG. 8B). Cells located at the edge of polystyrene-based microrafts (indicated by arrows in FIG. 8B) were partially shaded by the dark borders. When GR650F polysilsesquioxane was used to fabricate the microrafts, the dark border was eliminated or reduced because the refractive index of GR650F (n=1.42) is closer to that of PDMS and cell culture medium than the polystyrene (FIG. 8C). The better matching of refractive indices improved image quality in brightfield, and provides for an improved light throughput that permits a shorter integration time on a camera for capturing an image of acceptable quality.

Although specific embodiments have been illustrated and described herein, those of ordinary skill in the art appreciate that any arrangement which is calculated to achieve the same purpose may be substituted for the specific embodiments shown and that the invention has other applications in other environments. This application is intended to cover any adaptations or variations of the present invention. The following claims are in no way intended to limit the scope of the invention to the specific embodiments described herein.

We claim:

1. An apparatus for collecting or culturing cells or cell colonies, the apparatus comprising:
a substrate formed from a flexible resilient polymeric material and having a first surface and an opposed second surface and a plurality of wells formed in the first surface in the form of an array, the substrate having a refractive index; and
a plurality of micro-elements comprising a polysilsesquioxane polymer having a core structure $RSiO_{1.5}$ wherein R is methyl, methyl-phenyl or phenyl, wherein, each microelement releasably connected to the substrate in one of the wells, each microelement having a refractive index, the refractive index of each microelement is within about 10% of the refractive index of the substrate,
wherein the micro-elements are produced by a process of casting a single solvent solution of the polysilsesquioxane polymer in the wells.

2. The apparatus as recited in claim 1, wherein the micro-elements further comprise ferromagnetic particles.

3. The apparatus as recited in claim 2, wherein the single solvent is gamma-butyrolactone (GBL).

4. The apparatus as recited in claim 3, wherein the ratio of polysilsesquioxane:ferromagnetic particle:GBL is about 50:2.5:50 wt:wt:wt.

5. The apparatus as recited in claim 1, wherein the substrate comprises an elastomer.

6. The apparatus as recited in claim 5, wherein the elastomer is polydimethylsiloxane.

7. The apparatus as recited in claim 1, wherein the micro-elements are functionalized with a silane coupling reagent having the general formula R—Si(R')3, where R' can be one or more of OH, CI or alkoxyl and where R has a terminal functional group comprising an epoxide, amine, carboxyl, vinyl, mercapto, or imine.

8. The apparatus as recited in claim 7, wherein the micro-elements further comprise a covalently bound biologically or chemically active moiety.

9. The apparatus as recited in claim 1, comprising baking the micro-elements at a temperature of about 95° C. to evaporate the solvent.

10. The apparatus as recited in claim 1, wherein imaging of cells or cell colonies on the micro-elements produces a reduced shadowing around a perimeter of micro-elements as compared to imaging on micro-elements without a refractive index within about 10% of the refractive index of the substrate.

11. The apparatus as recited in claim 1, wherein the polysilsesquioxane has a degradation in spatial resolution of less than about 80% of a degradation from a polystyrene.

* * * * *